United States Patent [19]

Fujisawa et al.

[11] Patent Number: 5,595,882
[45] Date of Patent: Jan. 21, 1997

[54] ANGIOTENSIN II TYPE-1 RECEPTOR PROTEINS AND SCREENING ASSAYS USING SUCH PROTEINS OR TRANSFORMANTS EXPRESSING THEM

[75] Inventors: Yukio Fujisawa; Shun'ichi Kuroda, both of Kobe; Hiroaki Konishi, Ibaraki, all of Japan

[73] Assignee: Takeda Chemical Industries, Ltd., Osaka, Japan

[21] Appl. No.: 417,122

[22] Filed: Apr. 5, 1995

Related U.S. Application Data

[62] Division of Ser. No. 41,219, Mar. 31, 1993, Pat. No. 5,427,922.

[30] Foreign Application Priority Data

| Apr. 7, 1992 | [JP] | Japan | 4-85445 |
| Apr. 21, 1992 | [JP] | Japan | 4-101393 |
| Feb. 17, 1993 | [JP] | Japan | 5-27835 |

[51] Int. Cl.⁶ .................. C07K 14/72; G01N 33/566; C12Q 1/02
[52] U.S. Cl. .................. 435/7.21; 435/27; 435/69.1; 435/7.2; 530/350
[58] Field of Search .................. 530/350; 435/69.1, 435/7.21, 29, 7.2

[56] References Cited

U.S. PATENT DOCUMENTS 5,427,922  6/1995  Fujisawa et al. .................. 435/69.1

OTHER PUBLICATIONS

Furuta et al., Biochem. Biophys. Res. Commun., 183(1), 8 (1992).
Takayanagi et al., Biochem. Biophys. Res. Commun., 183(2), 910 (1992).
Murphy et al., Nature, 351, 233 (1991).
Sasaki et al., Nature, 351, 230 (1991).
Bergsma et al., "Cloning and Characterization of a Human Angiotensin II Type 1 Receptor", Biochem. Biophys. Res. Commun., 183(3), 989–995 (1992).
Kakar et al., "Angiotensin II Type-1 Receptor Subtype cDNAs: Differential Tissue Expression and Hormonal Regulation", Biochem. Biophys. Res. Commun., 183(3), 1090–1096 (1992).
Curnow et al., Mol. Endocrinol., 6, 1113–1118 (1992).
Sandberg et al., J. Biol. Chem., 267, 9455–9458 (1992).
Hahn et al., Biochem. Biophys. Res. Commun., 192(3), 1260–1265 (1993).

*Primary Examiner*—David L. Fitzgerald
*Attorney, Agent, or Firm*—Foley & Lardner

[57] ABSTRACT

The present invention relates to (1) a human angiotensin II type 1 receptor protein, a recombinant DNA containing a gene which codes for said protein, a transformant carrying said DNA, production of said protein, and anti-angiotensin II substance screening methods using transformants containing said protein.

13 Claims, 6 Drawing Sheets

FIG. 1

```
AGGTACCTTG ACAGGCAGCA GCGAAGTGAA CAGGACGTCA TGGACCGTCG CGCCGCTAGC
TAGCTACTTC GGGCCGTGGC GGTGATCGAT GGCGAGCGGC TGATGCGGAC CCTCGACGTT
AAGGGCGAGA GCCTGACGCG AGGCGGCGGT GCGGTAGACC CGACATAGAG CGCCTGTCTG
GGACGTACGA CGCCGTGCCG CTCTTATTAT ATAGTGTTTG ACAATCGACC AGGTGATCAA
TGATCCTCAA CTCTTCTACT GAAGATGGTA TTAAAAGAAT CCAAGATGAT TGTCCCAAAG
CTGGAAGGCA TAATTACATA TTTGTCATGA TTCCTACTTT ATACAGTATC ATCTTTGTGG
TGGGAATATT TGGAAACAGC TTGGTGGTGA TAGTCATTTA CTTTTATATG AAGCTGAAGA
CTGTGGCCAG TGTTTTTCTT TTGAATTTAG CACTGGCTGA CTTATGCTTT TTACTGACTT
TGCCACTATG GGCTGTCTAC ACAGCTATGG AATACCGCTG GCCCTTTGGC AATTACCTAT
GTAAGATTGC TTCAGCCAGC GTCAGTTTCA ACCTGTACGC TAGTGTGTTC CTACTCACGT
GTCTCAGCAT TGATCGATAC CTGGCTATTG TTCACCCAAT GAAGTCCCGC CTTCGACGCA
CAATGCTTGT AGCCAAAGTC ACCTGCATCA TCATTTGGCT GCTGGCAGGC TTGGCCAGTT
TGCCAGCTAT AATCCATCGA AATGTATTTT TCATTGAGAA CACCAATATT ACAGTTTGTG
CCTTCCATTA TGAGTCCCGA AATTCAACCC TCCCGATAGG GCTGGGCCTG ACCAAAAATA
TACTGGGTTC CTGTTTCCCT TTTCTGATCA TTCTTACAAG TTATACTCTT ATTTGGAAGG
CCCTAAAGAA GGCTTATGAA ATTCAGAAGA ACAACCCAAG AAATGATGAT ATTTTTAGGA
TAATTATGGC AATTGTGCTT TTCTTTTTCT TTTCCTGGAT TCCCCACCAA ATATTCACTT
TTCTGGATGT ATTGATTCAA CAGGGCATCA TACGTGACTG TAGAATTGCA GATATTGTGG
ACACGGCCAT GCCCATCACC ATTTGGATAG CTTATTTTAA CAATTGCCTG AATCCTCTGT
TTTATGGCTT TCTGGGAAAA AAATTTAAAA AGATATTCT CCAGCTTCTG AAATATATTC
CCCCAAAGGC CAAATCCCAC TCAAACCTTT CAACAAAAAT GAGCACGCTT TCCTACCGCC
CCTCAGATAA TGTAAGCTCA TCCACCAAGA AGCCTGCACC ATGTTTTGAG GTTGAGTGAC
ATGTTCGAAA CCTGCCATAA AGTAATTTTG TGAAAGAAGG AGCAAGAGAA CATTCCTCTG
CAGCACTTCA CTACCAAATG AGCCTTAGCT ACTTTTCAGA ATTTGAAGGA GAAATTGCAT
TTATGTGGAC TGAACCGACT TTTTCCTAAA GCTCTGAAAC AAAAAGCTTT TTCCTTTCCC
TTTTGCAACA AGACAAAGCA AAGCCACATT TTGCATTAGA CAGATGACGG CTGCTCGAAG
AACAATGTCA GA
```

FIG. 2A

Met Ile Leu Asn Ser Ser Thr Glu Asp Gly Ile Lys Arg Ile Gln Asp Cys
Pro Lys Ala Gly Arg His Asn Tyr Ile Phe Ile Pro Thr Leu Tyr Ser
Ile Ile Phe Val Val Gly Ile Phe Gly Asn Ser Leu Val Val Ile Val Tyr
Phe Tyr Met Lys Leu Lys Thr Val Ala Ser Val Phe Leu Leu Asn Leu Ala Leu
Ala Asp Leu Cys Phe Leu Leu Thr Leu Pro Leu Trp Ala Val Tyr Thr Ala Met
Glu Tyr Arg Trp Pro Phe Gly Asn Tyr Leu Cys Lys Ile Ala Ser Ala Ser Val
Ser Phe Asn Leu Tyr Ala Ser Val Phe Leu Leu Thr Cys Leu Ser Ile Asp Arg
Tyr Leu Ala Ile Val His Pro Met Lys Ser Arg Leu Arg Arg Thr Met Leu Val
Ala Lys Val Thr Cys Ile Ile Ile Trp Leu Leu Ala Gly Leu Ala Ser Leu Pro
Ala Ile Ile His Arg Asn Val Phe Phe Ile Glu Asn Thr Asn Ile Thr Val Cys

FIG. 2B

Ala Phe His Tyr Glu Ser Arg Asn Ser Thr Leu Pro Ile Gly Leu Gly Leu Thr
Lys Asn Ile Leu Gly Ser Cys Phe Pro Phe Leu Ile Ile Leu Thr Ser Tyr Thr
Leu Ile Trp Lys Ala Leu Lys Lys Ala Tyr Glu Ile Met Ala Ile Leu Gln Lys Asn Asn Pro Arg
Asn Asp Asp Ile Phe Arg Ile Ile Met Ala Ile Leu Val Leu Phe Phe Phe Ser
Trp Ile Pro His Gln Ile Gln Ile Ile Phe Thr Phe Leu Asp Val Leu Ile Gln Gly Ile
Ile Arg Asp Cys Arg Ile Ala Asp Ile Val Asp Thr Ala Met Pro Ile Thr Ile
Trp Ile Ala Tyr Phe Asn Asn Cys Leu Asn Pro Leu Phe Tyr Gly Phe Leu Gly
Lys Lys Phe Lys Lys Asp Ile Leu Leu Gln Leu Leu Lys Tyr Ile Pro Pro Lys Ala
Lys Ser His Ser Asn Leu Ser Thr Lys Met Ser Thr Leu Ser Tyr Arg Pro Ser
Asp Asn Val Ser Ser Ser Thr Lys Lys Pro Ala Pro Cys Phe Glu Val Glu

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 127 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: internal ( x i ) SEQUENCE DESCRIPTION: SEQ ID NO:1:

```
Arg Asn Ser Thr Leu Pro Ile Gly Leu Gly Leu Thr Lys Asn Ile Leu
 1               5                  10                  15
Gly Ser Cys Phe Pro Phe Leu Ile Ile Leu Thr Ser Tyr Thr Leu Ile
            20                  25                  30
Trp Lys Ala Leu Lys Lys Ala Tyr Glu Ile Gln Lys Asn Asn Pro Arg
        35                  40                  45
Asn Asp Asp Ile Phe Arg Ile Ile Met Ala Ile Val Leu Phe Phe Phe
    50                  55                  60
Phe Ser Trp Ile Pro His Gln Ile Phe Thr Phe Leu Asp Val Leu Ile
65                  70                  75                  80
Gln Gln Gly Ile Ile Arg Asp Cys Arg Ile Ala Asp Ile Val Asp Thr
                85                  90                  95
Ala Met Pro Ile Thr Ile Trp Ile Ala Tyr Phe Asn Asn Cys Leu Asn
            100                 105                 110
Pro Leu Phe Tyr Gly Phe Leu Gly Lys Lys Phe Lys Lys Asp Ile
            115                 120                 125
```

( 2 ) INFORMATION FOR SEQ ID NO:2:

( i ) SEQUENCE CHARACTERISTICS:
        ( A ) LENGTH: 381 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL:

( i v ) ANTI-SENSE:

( v i ) ORIGINAL SOURCE:
        ( A ) ORGANISM: Homo sapiens
        ( F ) TISSUE TYPE: Placental ( x i ) SEQUENCE DESCRIPTION: SEQ ID NO:2:

```
CGAAATTCAA CCCTCCCGAT AGGGCTGGGC CTGACCAAAA ATATACTGGG TTCCTGTTTC    60
CCTTTTCTGA TCATTCTTAC AAGTTATACT CTTATTTGGA AGGCCCTAAA GAAGGCTTAT   120
GAAATTCAGA AGAACAACCC AAGAAATGAT GATATTTTTA GGATAATTAT GGCAATTGTG   180
CTTTTCTTTT TCTTTTCCTG GATTCCCCAC CAAATATTCA CTTTTCTGGA TGTATTGATT   240
CAACAGGGCA TCATACGTGA CTGTAGAATT GCAGATATTG TGGACACGGC CATGCCCATC   300
```

| ACCATTTGGA | TAGCTTATTT | TAACAATTGC | CTGAATCCTC | TGTTTTATGG | CTTTCTGGGA | 360 |
| AAAAAATTTA | AAAAAGATAT | T | | | | 381 |

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL:

( i v ) ANTI-SENSE: NO ( x i ) SEQUENCE DESCRIPTION: SEQ ID NO:3:

| TTTSTGGTGG | GGATATTTGG | AAA | 23 |

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL:

( i v ) ANTI-SENSE: YES ( x i ) SEQUENCE DESCRIPTION: SEQ ID NO:4:

| GTAGCGGTCR | ATGCTKAGAC | 20 |

( 2 ) INFORMATION FOR SEQ ID NO:5:

( i ) SEQUENCE CHARACTERISTICS:
        ( A ) LENGTH: 1572 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens
        ( F ) TISSUE TYPE: Placental ( x i ) SEQUENCE DESCRIPTION: SEQ ID NO:5:

| AGGTACCTTG | ACAGGCAGCA | GCGAAGTGAA | CAGGACGTCA | TGGACCGTCG | CGCCGCTAGC | 60 |
| TAGCTACTTC | GGGCCGTGGC | GGTGATCGAT | GGCGAGCGGC | TGATGCGGAC | CCTCGACGTT | 120 |
| AAGGGCGAGA | GCCTGACGCG | AGGCGGCGGT | GCGGTAGACC | CGACATAGAG | CGCCTGTCTG | 180 |
| GGACGTACGA | CGCCGTGCCG | CTCTTATTAT | ATAGTGTTTG | ACAATCGACC | AGGTGATCAA | 240 |
| TGATCCTCAA | CTCTTCTACT | GAAGATGGTA | TTAAAAGAAT | CCAAGATGAT | TGTCCCAAAG | 300 |
| CTGGAAGGCA | TAATTACATA | TTTGTCATGA | TTCCTACTTT | ATACAGTATC | ATCTTTGTGG | 360 |
| TGGGAATATT | TGGAAACAGC | TTGGTGGTGA | TAGTCATTTA | CTTTTATATG | AAGCTGAAGA | 420 |
| CTGTGGCCAG | TGTTTTTCTT | TTGAATTTAG | CACTGGCTGA | CTTATGCTTT | TTACTGACTT | 480 |
| TGCCACTATG | GGCTGTCTAC | ACAGCTATGG | AATACCGCTG | GCCCTTTGGC | AATTACCTAT | 540 |
| GTAAGATTGC | TTCAGCCAGC | GTCAGTTTCA | ACCTGTACGC | TAGTGTGTTC | CTACTCACGT | 600 |

5,595,882

-continued

| GTCTCAGCAT | TGATCGATAC | CTGGCTATTG | TTCACCCAAT | GAAGTCCCGC | CTTCGACGCA | 660 |
| CAATGCTTGT | AGCCAAAGTC | ACCTGCATCA | TCATTTGGCT | GCTGGCAGGC | TTGGCCAGTT | 720 |
| TGCCAGCTAT | AATCCATCGA | AATGTATTTT | TCATTGAGAA | CACCAATATT | ACAGTTTGTG | 780 |
| CCTTCCATTA | TGAGTCCCGA | AATTCAACCC | TCCCGATAGG | GCTGGGCCTG | ACCAAAAATA | 840 |
| TACTGGGTTC | CTGTTTCCCT | TTTCTGATCA | TTCTTACAAG | TTATACTCTT | ATTTGGAAGG | 900 |
| CCCTAAAGAA | GGCTTATGAA | ATTCAGAAGA | ACAACCCAAG | AAATGATGAT | ATTTTTAGGA | 960 |
| TAATTATGGC | AATTGTGCTT | TTCTTTTTCT | TTTCCTGGAT | TCCCCACCAA | ATATTCACTT | 1020 |
| TTCTGGATGT | ATTGATTCAA | CAGGGCATCA | TACGTGACTG | TAGAATTGCA | GATATTGTGG | 1080 |
| ACACGGCCAT | GCCCATCACC | ATTTGGATAG | CTTATTTTAA | CAATTGCCTG | AATCCTCTGT | 1140 |
| TTTATGGCTT | TCTGGGAAAA | AAATTTAAAA | AAGATATTCT | CCAGCTTCTG | AAATATATTC | 1200 |
| CCCCAAAGGC | CAAATCCCAC | TCAAACCTTT | CAACAAAAAT | GAGCACGCTT | TCCTACCGCC | 1260 |
| CCTCAGATAA | TGTAAGCTCA | TCCACCAAGA | AGCCTGCACC | ATGTTTTGAG | GTTGAGTGAC | 1320 |
| ATGTTCGAAA | CCTGCCATAA | AGTAATTTTG | TGAAAGAAGG | AGCAAGAGAA | CATTCCTCTG | 1380 |
| CAGCACTTCA | CTACCAAATG | AGCCTTAGCT | ACTTTTCAGA | ATTTGAAGGA | GAAATTGCAT | 1440 |
| TTATGTGGAC | TGAACCGACT | TTTTCCTAAA | GCTCTGAAAC | AAAAAGCTTT | TTCCTTTCCC | 1500 |
| TTTTGCAACA | AGACAAAGCA | AAGCCACATT | TTGCATTAGA | CAGATGACGG | CTGCTCGAAG | 1560 |
| AACAATGTCA | GA | | | | | 1572 |

( 2 ) INFORMATION FOR SEQ ID NO:6:

( i ) SEQUENCE CHARACTERISTICS:
( A ) LENGTH: 359 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: Homo sapiens
( F ) TISSUE TYPE: Placental ( x i ) SEQUENCE DESCRIPTION: SEQ ID NO:6:

```
Met Ile Leu Asn Ser Ser Thr Glu Asp Gly Ile Lys Arg Ile Gln Asp
 1               5                  10                  15

Asp Cys Pro Lys Ala Gly Arg His Asn Tyr Ile Phe Val Met Ile Pro
                20                  25                  30

Thr Leu Tyr Ser Ile Ile Phe Val Val Gly Ile Phe Gly Asn Ser Leu
            35                  40                  45

Val Val Ile Val Ile Tyr Phe Tyr Met Lys Leu Lys Thr Val Ala Ser
     50                  55                  60

Val Phe Leu Leu Asn Leu Ala Leu Ala Asp Leu Cys Phe Leu Leu Thr
 65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
                100                 105                 110

Tyr Ala Ser Val Phe Leu Leu Thr Cys Leu Ser Ile Asp Arg Tyr Leu
            115                 120                 125

Ala Ile Val His Pro Met Lys Ser Arg Leu Arg Arg Thr Met Leu Val
        130                 135                 140

Ala Lys Val Thr Cys Ile Ile Ile Trp Leu Leu Ala Gly Leu Ala Ser
145                 150                 155                 160
```

| | | | | | | | | | | | | | | |
|---|---|---|---|---|---|---|---|---|---|---|---|---|---|---|
| Leu | Pro | Ala | Ile | Ile 165 | His | Arg | Asn | Val | Phe 170 | Phe | Ile | Glu | Asn | Thr 175 | Asn |
| Ile | Thr | Val | Cys 180 | Ala | Phe | His | Tyr | Glu 185 | Ser | Arg | Asn | Ser | Thr 190 | Leu | Pro |
| Ile | Gly | Leu 195 | Gly | Leu | Thr | Lys | Asn 200 | Ile | Leu | Gly | Ser | Cys 205 | Phe | Pro | Phe |
| Leu | Ile 210 | Ile | Leu | Thr | Ser | Tyr 215 | Thr | Leu | Ile | Trp | Lys 220 | Ala | Leu | Lys | Lys |
| Ala 225 | Tyr | Glu | Ile | Gln | Lys 230 | Asn | Asn | Pro | Arg | Asn 235 | Asp | Asp | Ile | Phe | Arg 240 |
| Ile | Ile | Met | Ala | Ile 245 | Val | Leu | Phe | Phe | Phe 250 | Phe | Ser | Trp | Ile | Pro 255 | His |
| Gln | Ile | Phe | Thr 260 | Phe | Leu | Asp | Val | Leu 265 | Ile | Gln | Gln | Gly | Ile 270 | Ile | Arg |
| Asp | Cys | Arg 275 | Ile | Ala | Asp | Ile | Val 280 | Asp | Thr | Ala | Met | Pro 285 | Ile | Thr | Ile |
| Trp | Ile 290 | Ala | Tyr | Phe | Asn | Asn 295 | Cys | Leu | Asn | Pro | Leu 300 | Phe | Tyr | Gly | Phe |
| Leu 305 | Gly | Lys | Lys | Phe | Lys 310 | Lys | Asp | Ile | Leu | Gln 315 | Leu | Leu | Lys | Tyr | Ile 320 |
| Pro | Pro | Lys | Ala | Lys 325 | Ser | His | Ser | Asn | Leu 330 | Ser | Thr | Lys | Met | Ser 335 | Thr |
| Leu | Ser | Tyr | Arg 340 | Pro | Ser | Asp | Asn | Val 345 | Ser | Ser | Ser | Thr | Lys 350 | Lys | Pro |
| Ala | Pro | Cys 355 | Phe | Glu | Val | Glu | | | | | | | | | |

ANGIOTENSIN II TYPE-1 RECEPTOR PROTEINS AND SCREENING ASSAYS USING SUCH PROTEINS OR TRANSFORMANTS EXPRESSING THEM

This application is a division, of application Ser. No. 08/041,219, filed Mar. 31, 1993, now U.S. Pat. No. 5,427, 922.

FIELD OF THE INVENTION

The present invention relates to a new human angiotensin II type 1 receptor, a recombinant DNA which codes therefor, a transformant carrying said recombinant DNA, a method of producing said receptor, and a use therefor. More specifically, the present invention provides a method of accurately assaying the bioactivities of angiotensin II antagonists and agonists, in a pure system containing substantially no other receptors, by expressing a human angiotensin II type 1 receptor gene in an animal cell using recombinant DNA technology.

BACKGROUND OF THE INVENTION

The renin-angiotensin (RA) system, essential to the regulation of blood pressure and aqueous electrolytes in vivo, plays a key role in various hypertensive diseases, congestive heart failure and edematous diseases.

Renin, produced mainly in the renal juxtaglomerular apparatus, acts on angiotensinogen, present in the blood, kidney and other organs, to produce angiotensin (Ang) I. Ang I possesses almost no bioactivity and, upon action of angiotensin-converting enzyme (ACE), is converted to a bioactive form known as Ang II. Ang II is thought to make a most significant contribution to the bioactivity of the RA system, though Ang III is also produced by the same system. The amino acid number of Ang III is lower by 1 than that of Ang II, and its bioactivity is similar to that of Ang II.

The most important action of Ang II is its cardiovascular action, its peripheral vasoconstrictive action being very potent and playing a major role in the maintenance of blood pressure. In addition to this action, Ang II has proven to be active on the adrenal zona glomerulosa to induce aldosterone production and on the adrenal medulla and sympathetic nerve ends to promote catecholamine secretion, vasopressin secretion and prostaglandin E2 and I2 production, and is involved in the glomerular filtering function and the renal uriniferous tubular sodium reabsorption mechanism. Since renin and Ang II are also produced in the brain, heart, vascular wall, adrenal and other non-kidney organs, the local action thereof as produced in these ectopic RA systems is drawing attention, as are the above physiological actions.

Since the RA system owes its bioactivity mainly to Ang II, as stated above, it has been believed that the above-mentioned diseases can be prevented or mitigated by suppressing Ang II production and hence the RA system. To inhibit the renin production, which is the starting material of the RA system, β-blockers have long been used. However, since β-blockers possess a broad range of action points, focus has recently been on the development of renin inhibitors, which are unsatisfactory in absorption via the digestive tract; no drug permitting practical application has been developed. Currently widely used RA system inhibitors are ACE inhibitors, exemplified by captopril, enalapril, delapril and alacepril. Although these drugs are already in practical application for their excellent effect, they have side effects, such as dry cough and diuresis, as a result of increase in bradykinin and prostaglandin levels, because they also suppress kininase II. Therefore the development of an Ang II receptor antagonist has been desired as a drug which suppresses only Ang II bioactivity.

Orally administrable non-peptide Ang II receptor antagonists have long been studied. For example, imidazole acetate series compounds have been studied for diuretic and hypotensive action since around 1976, and CV-2961 and other compounds have been found to possess Ang II receptor antagonist activity [Y. Furukawa et al., U.S. Pat. No. 4,340, 598 (1982); Y. Furukawa et al., U.S. Pat. No. 4,355,040 (1982)], as the result. Since then, there have been improvements in these compounds, resulting in the development of DuP 753 [A. T. Chiu et al., Journal of Pharmacology and Experimental Therapeutics, 252, 711 (1990)]. DuP 753 proved to act specifically on Ang II receptors in the vascular wall, adrenal cortex and other organs to suppress Ang II action only. It was also shown to have no effect on reactions of KCl, norepinephrine, isoproterenol, vasopressin, bradykinin, acetylcholine or 5-HT, or on ACE action, even at suppressive doses for a high concentration (10 μM) of Ang II [P. C. Wong et al., J. Pharmacol. Exp. Ther., 252, 719 (1990)]. According to the recognition of such pharmacological utility of non-peptide antagonists for Ang II receptors, the studies of Ang II receptors has been increased. It is conjectured that there are at least two kinds of Ang II receptor, according to reactivity to antagonists: type 1 receptors, to which DuP 753 is antagonistic, and type 2 receptors, to which PD123177 is antagonistic [P.B.M.W.M. Timmermans et al., Trends in Pharmaceutical Science (TiPS), 12, 55 (1991)], of which type 1 receptors are thought to play a key role in known Ang II-dependent diseases.

Thus development of Ang II type 1 receptor antagonists has been brisk. To accurately assess the antagonist activity of a drug, it is necessary to use cells or cell membrane fraction having Ang II type 1 receptors only. However, the receptors used in these studies are based on membrane fractions derived from laboratory animals (e.g., bovines, rats), which contain various receptors other than the desired Ang II receptor. For this reason, there is a need for preparing cells which specifically express human Ang II type 1 receptors and the use of such cells or cell membrane fractions to accurately determine the bioactivity of the antagonist in a pure system.

SUMMARY OF THE INVENTION

The present inventors have succeeded in cloning a gene from a cDNA library derived from the human placenta which shares high homology with known human, bovine and rat Ang II type 1 receptor genes but which has a new nucleotide sequence. The inventors expressed this clone in an animal cell and found that the clone can serve as an Ang II type 1 receptor. Assuming that the receptor thus obtained is an Ang II type 1 receptor of human origin different from any known Ang II type 1 receptor of human origin, the inventors made further investigations based on the above findings and developed the present invention.

Accordingly, the present invention comprises (1) synthesizing a primer for amplifying a well-conserved region, based on the reported sequences for the Ang II type 1 receptor derived from bovine adrenal zona glomerulosa cells [K. Sasaki et al., Nature, 351, 230 (1991)] and for the Ang II type 1 receptor derived from rat aortic smooth muscle cells [T. J. Murphy et al., Nature, 351, 233 (1991)], (2) amplifying the well-conserved region from a cDNA library derived from the human placenta by PCR using said primer, (3) subcloning of the amplified DNA into a vector, (4) identifying the region which codes for the human Ang II type 1 receptor from the subcloned DNA, (5) obtaining a novel Ang II type 1 receptor gene of human origin by plaque hybridization using said coding sequence as a probe, (6)

preparing a recombinant DNA for expressing the gene of (5) above in a host cell, (7) preparing a transformant carrying the recombinant DNA of (6) above, (8) obtaining the Ang II type 1 receptor of human origin by culturing the transformant of (7) above, (9) determining the bioactivity of a receptor antagonist using all or part (e.g., cell membrane) of the transformant of (7) above, and (10) determining the activity of the Ang II type 1 receptor of human origin using the transformant of (7) above.

BRIEF DESCRIPTION OF THE DRAWINGS

FIG. 1 shows the nucleotide sequence of the Ang II type 1 receptor gene, derived from human placenta, contained in the plasmid pHARp116 (see Example 3).

FIGS. 2A–2B show the amino acid sequence deduced from the Ang II type 1 receptor gene, derived from human placenta, contained in the plasmid pHARp116 (see Example 3).

DETAILED DESCRIPTION OF THE INVENTION

Figure 3:
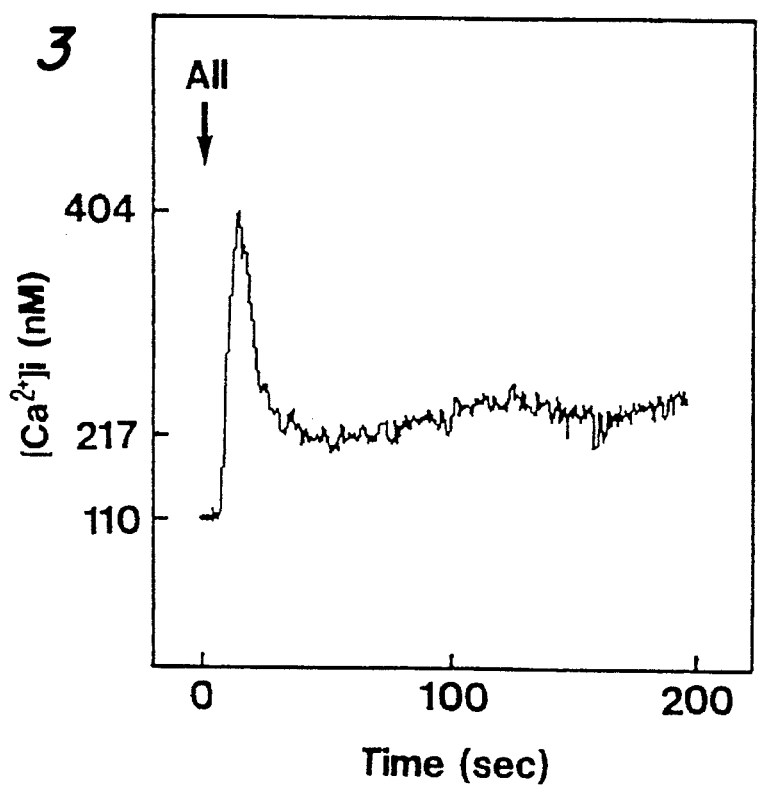
FIG. 3 shows changes in intracellular calcium ion concentration in response to stimulation with Ang II in full-length heart-derived Ang II type 1 receptor expressing cells (see Example 11).

The present invention provides:

(1) a new polypeptide in a new human Ang II type 1 receptor, i.e., polypeptide (I) comprising the amino acid sequence represented by the following formula I:

Arg—Asn—Ser—Thr—Leu—Pro—Ile—Gly—Leu—Gly—Leu—Thr—Lys—Asn—Ile—Leu—Gly—Ser— (SEQ ID No. 1)

Cys—Phe—Pro—Phe—Leu—Ile—Ile—Leu—Thr—Ser—Tyr—Thr—Leu—Ile—Trp—Lys—Ala—Leu—

Lys—Lys—Ala—Tyr—Glu—Ile—Gln—Lys—Asn—Asn—Pro—Arg—Asn—Asp—Asp—Ile—Phe—Arg—

Ile—Ile—Met—Ala—Ile—Val—Leu—Phe—Phe—Phe—Phe—Ser—Trp—Ile—Pro—His—Gln—Ile—

Phe—Thr—Phe—Leu—Asp—Val—Leu—Ile—Gln—Gln—Gly—Ile—Ile—Arg—Asp—Cys—Arg—Ile—

Ala—Asp—Ile—Val—Asp—Thr—Ala—Met—Pro—Ile—Thr—Ile—Trp—Ile—Ala—Tyr—Phe—Asn—

Asn—Cys—Leu—Asn—Pro—Leu—Phe—Tyr—Gly—Phe—Leu—Gly—Lys—Lys—Phe—Lys—Lys—Asp—

Ile, (2) a recombinant DNA (A) which encodes polypeptide (I), (3) a transformant (B) carrying a vector comprising said recombinant DNA (A), (4) a method of producing polypeptide (I) wherein transformant (B) is cultured in a medium to produce and accumulate polypeptide (I), which is then harvested, (5) a method of screening an anti-angiotensin II substance, which comprises, in the presence of angiotensin II and the polypeptide (I), identifying a substance capable of inhibiting angiotensin II from binding to said polypeptide.

(6) A method of screening an angiotensin II type 1 receptor ligand which comprises identifying a Substance capable of binding the polypeptide (I).

(7) A method of screening an anti-angiotensin II substance, which comprises, in the presence of the transformant (B) which contains the polypeptide (I) and angiotensin II, identifying a substance capable of suppressing change of a concentration of an angiotensin II responsive substance intracellularly in response angiotensin II existing in said transformant.

(8) A method of screening an angiotensin II type 1 receptor agonist which comprises identifying a substance capable of changing a concentration of an angiotensin II responsive substance intracellularly in the transformant (B) which consists the polypeptide (I).

Any polypeptide can serve as polypeptide (I), as long as it is capable of receiving human Ang II, i.e. specifically binds to ligands capable of binding to human Ang II type 1 receptors, such as human Ang II antagonists and agonists for human Ang II type 1 receptor, and induces activation of intracellular substances (e.g., Ca ions) or behavior change by the resulting structural change, and contains the amino acid sequence represented by the above formula (I) (SEQ ID No. 1). Such polypeptides include (1) human Ang II type 1 receptor comprising the amino acid sequence shown in FIGS. 2A–2B (SEQ ID No. 6), and (2) human Ang II type 1 receptor muteins such as proteins resulting from deletion or replacement of one or more of the amino acids at the 1–186 and 314–359 positions in the amino acid sequence shown in FIGS. 2A–2B, and proteins resulting from addition of one or more amino acids to the N terminal or C terminal of the amino acid sequence shown in FIGS. 2A–2B, with preference given to human Ang II type 1 receptor represented by the amino acid sequence shown in FIGS. 2A–2B (SEQ ID No. 6).

Any DNA can serve as the recombinant DNA (A), as long as it contains a nucleotide sequence which codes for the amino acid sequence represented by formula I, whether part or all of the sequence is derived from a natural source or chemical synthesis, or combination of them.

Any nucleotide sequence can serve to code for the amino acid sequence represented by formula I, with preference given to the nucleotide sequence represented by the following formula II:

5'-CGAAATTCAACCCTCCCGATAGGGCTGGGCCTGACCAAAAATATACTGGGTTCCTGTTTCCCTTTTCTG (SEQ ID No. 2)

ATCATTCTTACAAGTTATACTCTTATTTGGAAGGCCCTAAAGAAGGCTTATGAAATTCAGAAGAACAACCCA

AGAAATGATGATATTTTTAGGATAATTATGGCAATTGTGCTTTTCTTTTTCTTTTCCTGGATTCCCCACCAA

ATATTCACTTTTCTGGATGTATTGATTCAACAGGGCATCATACGTGACTGTAGAATTGCAGATATTGTGGAC

ACGGCCATGCCCATCACCATTTGGATAGCTTATTTTAACAATTGCCTGAATCCTCTGTTTTATGGCTTTCTG

GGAAAAAAATTTAAAAAAGATATT-3'

Recombinant DNA (A) is preferably the DNA represented by the nucleotide sequence shown in FIG. 1 (SEQ ID No. 5). Any nucleotide sequence can serve to code for the human Ang II type 1 receptor represented by the amino acid sequence shown in FIGS. 2A–2B, with preference given to the nucleotide sequence represented by the following formula (which is same as the nucleotides at the 240–1316 positions in the nucleotide sequence shown in FIG. 1):

RNA which codes for a human Ang II type 1 receptor can be obtained from various human organs and cells. Methods of preparing RNA from these materials include the guanidine thiocyanate method [J. M. Chirgwin et al., Biochemistry, 18, 5294 (1979)].

5'-ATGATCCTCAACTCTTCTACTGAAGATGGTATTAAAAGAATCCAAGATGATTGTCCCAAAGCTGGAA

GGCATAATTACATATTTGTCATGATTCCTACTTTATACAGTATCATCTTTGTGGTGGGAATATTTGGAAA

CAGCTTGGTGGTGATAGTCATTTACTTTTATATGAAGCTGAAGACTGTGGCCAGTGTTTTTCTTTTGAAT

TTAGCACTGGCTGACTTATGCTTTTTACTGACTTTGCCACTATGGGCTGTCTACACAGCTATGGAATACC

GCTGGCCCTTTGGCAATTACCTATGTAAGATTGCTTCAGCCAGCGTCAGTTTCAACCTGTACGCTAGTGT

GTTCCTACTCACGTGTCTCAGCATTGATCGATACCTGGCTATTGTTCACCCAATGAAGTCCCGCCTTCGA

CGCACAATGCTTGTAGCCAAAGTCACCTGCATCATCATTTGGCTGCTGGCAGGCTTGGCCAGTTTGCCAG

CTATAATCCATCGAAATGTATTTTTCATTGAGAACACCAATATTACAGTTTGTGCCTTCCATTATGAGTC

CCGAAATTCAACCCTCCCGATAGGGCTGGGCCTGACCAAAAATATACTGGGTTCCTGTTTCCCTTTTCTG

ATCATTCTTACAAGTTATACTCTTATTTGGAAGGCCCTAAAGAAGGCTTATGAAATTCAGAAGAACAACC

CAAGAAATGATGATATTTTTAGGATAATTATGGCAATTGTGCTTTTCTTTTTCTTTTCCTGGATTCCCCA

CCAAATATTCACTTTTCTGGATGTATTGATTCAACAGGGCATCATACGTGACTGTAGAATTGCAGATATT

GTGGACACGGCCATGCCCATCACCATTTGGATAGCTTATTTTAACAATTGCCTGAATCCTCTGTTTTATG

GCTTTCTGGGAAAAAAATTTAAAAAAGATATTCTCCAGCTTCTGAAATATATTCCCCCAAAGGCCAAATC

CCACTCAAACCTTTCAACAAAAATGAGCACGCTTTCCTACCGCCCCTCAGATAATGTAAGCTCATCCACC

AAGAAGCCTGCACCATGTTTTGAGGTTGAG-3'

A vector harboring recombinant DNA containing a gene which codes for the human Ang II type 1 (hAT$_1$) receptor of the present invention can, for example, be produced by:
(a) separating RNA which codes for the hAT$_1$ receptor,
(b) synthesizing single-stranded complementary DNA (cDNA) from said RNA and then double-stranded DNA,
(c) incorporating said double-stranded DNA to an appropriate plasmid,
(d) transforming an appropriate host with the resulting recombinant plasmid,
(e) culturing the resulting transformant and then isolating the plasmid containing the desired DNA therefrom by an appropriate method (e.g., colony hybridization using a DNA probe),
(f) cleaving out the desired cloned DNA from the plasmid, and
(g) ligating said cloned DNA to the downstream of an appropriate promoter in a vehicle.

The cDNA can also be produced by chemical synthesis.

After adding an oligo-dT primer or random oligonucleotide to the thus-obtained RNA, reverse transcriptase may be added to synthesize cDNA [H. Okayama et al., Molecular and Cellular Biology, 2, 161 (1982) and 3, 280 (1983)]. To this cDNA preparation, sense primer and antisense primer (see Examples below) may be added to amplify a well-conserved region, based on the reported sequences for the Ang II type 1 receptor from bovine adrenal zona glomerulosa cells [K. Sasaki et al., Nature, 351, 230 (1991)] and for the Ang II type 1 receptor from rat aortic smooth muscle cells [T. J. Murphy et al., Nature, 351, 233 (1991)]. Then, a polymerase chain reaction (PCR) may be carried out using a commercially available kit (e.g., a kit produced by Cetus/Perkin-Elmer). The amplified cDNA can be separated by a known method such as agarose electrophoresis and then recovered from the gel. The nucleotide sequence of this cDNA can be determined by, for example, the "dideoxy" chain termination method [T. Messing et al., Nucleic Acids Research, 9, 309 (1981)].

The plasmid having the cloned cDNA may be used as such or after being cleaved with appropriate restriction enzyme and inserted to another vector (e.g., plasmid) as necessary.

Examples of the plasmid for cDNA insertion include plasmids derived from *Escherichia coli* such as pBR322 [Gene, 2, 95 (1977)], pBR325 [Gene, 4, 121 (1978)], pUC12 [Gene, 19, 259 (1982)], pUC13 [Gene, 19, 9, 259 (1982)], pUC118 and pUC119 [Methods in Enzymology, 153, 3–11 (1987)] and those derived from *Bacillus subtilis* such as pUB110 [Biochemical and Biophysical Research Communications, 112, 678 (1983)], but any other can be used for this purpose, as long as it is replicable and retainable in the host.

Examples of the method of insertion to the plasmid include that described by T. Maniatis et al. in Molecular Cloning, Cold Spring Harbor Laboratory, page 239 (1982).

The plasmid incorporating said cDNA may be a plasmid obtained using a cDNA library (with *Escherichia coli* x1776) host prepared by inserting a cDNA synthesized from human normal diploid cell mRNA to the pCD vector [see Okayama et al., Molecular Cell Biology, 3, 280 (1983)], which cDNA library was given from Dr. Okayama at the Research Institute for Microbial Diseases, Osaka University.

The plasmid thus obtained is introduced to an appropriate host such as a bacterium of the genus Escherichia or Bacillus.

Exemplary bacteria of the genus Escherichia include *Escherichia coli* K12DH1 [Proceedings of the National Academy of Science, USA, 60, 160 (1968)], M103 [Nucleic Acids Research, 9, 309 (1981)], JM109 [Methods in Enzymology, 153, 3–11 (1987)], JA221 [Journal of Molecular Biology, 120, 517 (1978)], HB101 [Journal of Molecular Biology, 41, 459 (1969)], C600 [Genetics, 39, 440 (1954)] and MC1061/P3 [Nature, 329, 840 (1987)].

Example bacteria of the genus Bacillus include *Bacillus subtilis* MI114 [Gene, 24, 255 (1983)] and 207–21 [Journal of Biochemistry, 95, 87 (1984)].

Methods of transformation include the calcium chloride method and calcium chloride/rubidium chloride method described by T. Maniatis in Molecular Cloning, Cold Spring Harbor Laboratory, page 249 (1982).

From the transformants thus obtained, the desired clone is selected using a known method, such as colony hybridization [Gene, 10, 63 (1980)] or DNA nucleotide sequencing [Proceedings of the National Academy of Science, USA, 74, 560 (1977); Nucleic Acids Research, 9, 309 (1981)].

A microorganism carrying a vector containing a nucleotide sequence which codes for the cloned $hAT_1$ receptor is thus obtained.

Next, the plasmid is isolated from the microorganism. Methods of such isolation include the alkali method [H. C. Birmboim et al., Nucleic Acids Research, 1, 1513 (1979)].

The above vector containing a gene which codes for the cloned $hAT_1$ receptor can be used as such or after being cleaved out with a restriction enzyme as necessary.

The cloned gene is joined to the downstream of the promoter, in a vehicle (vector) suitable for its expression, to yield an expression vector.

Exemplary vectors include the above-mentioned plasmids derived from *Escherichia coli* (e.g., pBR322, pBR325, pUC12, pUC13, pUC118, pUC119), plasmids derived from *Bacillus subtilis* (e.g., pUB110, pTP5, pC194), yeast-derived plasmids (e.g., pSH19, pSH15), bacteriophages such as λ phage, animal viruses such as retrovirus and vaccinia virus and plasmids for animal cell expression (e.g., pcDNA I).

The gene may have ATG (nucleotide sequence which codes for an appropriate signal peptide as desired) as a translational initiation codon at its 5'-terminal and TAA, TGA or TAG (preferably TGA) as a translational termination codon at its 3'-terminal. To express the gene, a promoter is ligated to the upstream thereof. Any promoter can be used for the present invention, as long as it is appropriate for the host used to express the gene. Examples of preferred promoters are given below.

Preferred promoters include the T7 promoter, trp promoter, lac promoter, rec A promoter, $\lambda P_L$ promoter and lpp promoter, when the transformation host belongs to the genus Escherichia; the SPO1 promoter, SPO2 promoter and pen P promoter when the host belongs to Bacillus; and the PHO5 promoter, PGK promoter, GAPDH promoter and ADH promoter when the host is a yeast. Preference is given to the case in which a bacterium of the genus Escherichia is used as host in combination with the trp promoter or T7 promoter. When the host is an animal cell, preferable promoters include the SV40-derived promoter, retrovirus promoter and human cytomegalovirus promoter, with preference given to the SV40-derived promoter.

The thus-constructed expression vector, containing a gene encoding an $hAT_1$ receptor, is used to produce a transformant. Examples of the host include bacteria of the genus Escherichia, bacteria of the genus Bacillus, yeasts and animal cells, with preference given to animal cells. Examples of the bacteria of the genus Escherichia and of the genus Bacillus include the same as specified above. Especially, the host is preferably an animal cell, when the transformant cells are used for screening an agonist or an antagonist of the $hAT_1$ receptor as described below.

Examples of the yeasts include *Saccharomyces cerevisiae* AH22R-, NA87-11A and DKD-5D. Exemplary animal cells include simian cells COS-7, Vero, Chinese hamster ovary (CHO) cells, mouse L cells, mouse myeloma Sp2/O cells and human FL cells.

The bacteria of the genus Escherichia can be transformed in accordance with the method described in the Proceedings of the National Academy of Science, USA, 69, 2110 (1972), Gene, 17, 107 (1982), for instance. Bacteria of the genus Bacillus can be transformed in accordance with the method described in Molecular and General Genetics, 168, 111 (1979), for instance. Yeasts can be transformed in accordance with the method described in the Proceedings of the National Academy of Science, USA, 75, 1929 (1978), for instance. Animal cells can be transformed in accordance with the method described in Virology, 52, 456 (1973), for instance.

A transformant resulting from transformation with a vector harboring the cDNA of $hAT_1$ receptor is thus obtained.

For cultivating a transformant whose host is a bacterium of the genus Escherichia or Bacillus, it is appropriate to use a liquid medium supplemented with carbon sources, nitrogen sources, minerals and other substances necessary for transformant growth. Examples of carbon sources include glucose, dextrin, soluble starch and sucrose. Examples of nitrogen sources include organic or inorganic substances such as ammonium salts, nitrates, corn steep liquor, peptone, casein, meat extract, soybean cake and potato extract. Examples of minerals include calcium chloride, sodium dihydrogen phosphate and magnesium chloride. Yeast extract, vitamins, growth factors and other additives may be added. The pH of the medium is preferably about 6 to 8.

Examples of media preferably used to cultivate the genus Escherichia include M9 medium containing glucose and Casamino acid [Miller, Journal of Experiments in Molecular Genetics, 431–433, Cold Spring Harbor Laboratory, New York (1972)]. To increase promoter efficiency as necessary, a chemical agent such as 3β-indolyl acrylic acid may be added.

When the host is a bacterium of the genus Escherichia, cultivation is normally carried out at about 15° to 43° C. for about 3 to 24 hours, with aeration and/or stirring as necessary.

When the host is a bacterium of the genus Bacillus, cultivation is normally carried out at about 30° to 40° C. for about 6 to 24 hours, with aeration and/or stirring as necessary.

Examples of media for cultivating a transformant whose host is a yeast include Burkholder's minimal medium [Bostian, K. L. et al., Proceedings of the National Academy of Science, USA, 77, 4505 (1980)]. The preferable pH of the medium is pH of about 5 to 8. Cultivation is normally carried out at about 20° to 35° C. for about 24 to 72 hours, with aeration and/or stirring as necessary.

Examples of media for cultivating a transformant whose host is an animal cell include MEM medium [Science, 122, 501 (1952)], DMEM medium [Virology, 8, 396 (1959)], RPMI 1640 medium [Journal of the American Medical Association, 199, 519 (1967)], 199 medium [Proceedings of the Society for the Biological Medicine, 73, 1 (1950)] and ASF104 (produced by Ajinomoto). These media may be supplemented with about 5 to 20% fetal bovine serum. The pH is preferably about 6 to 8. Cultivation is normally carried out at about 30° to 40° C. for about 15 to 60 hours, with aeration and/or stirring as necessary.

Separation and purification of the $hAT_1$ receptor of the present invention from the culture described above can, for example, be achieved as follows:

In extracting the $hAT_1$ receptor of the present invention from cultured cells, the cells are collected by a known method after cultivation and suspended in a buffer containing a protein denaturant, such as guanidine hydrochloride, to elute the desired $hAT_1$ receptor from the cells. In another method, the cells are disrupted by ultrasonication, lysozyme treatment and/or freeze-thawing, after which they are centrifuged to separate the receptor of the invention. The method using a combination of lysozyme treatment and ultrasonication is preferred.

For purifying the receptor of the present invention from the supernatant, known methods of separation and purification can be used in combination as appropriate. Such known methods of separation and purification include those based on solubility differences such as salting-out and solvent precipitation, those based mainly on molecular weight differences such as dialysis, ultrafiltration, gel filtration and SDS-polyacrylamide gel electrophoresis, those based on charge differences such as ion exchange chromatography, those based on specific affinity such as affinity chromatography, those based on hydrophobicity differences such as reverse-phase high performance liquid chromatography, and those based on isoelectric point differences such as isoelectric focusing.

The thus-obtained $hAT_1$ receptor of the present invention may be prepared as a dry powder by dialysis, lyophilization and other treatments. It is appropriate to add serum albumin etc. as a carrier in storing the $hAT_1$ receptor, since its adsorption to the container is prevented.

The $hAT_1$ receptor of the present invention is thus obtained, in a substantially pure form. The substantially pure protein of the present invention has a protein content of not less than 95% (w/w), preferably not less than 98% (w/w).

The $hAT_1$ receptor thus obtained, the cells containing, specifically expressing, the receptor, cell membrane preparations therefrom, or the like can be used for screening of substances exhibiting antagonist or agonist activity against the $hAT_1$ receptor, in which the amount of ligand bound to the $hAT_1$ receptor is determined in a ligand binding test, for instance. Especially, it is suitable for identifying an anti-Ang II substance which inhibits the binding of Ang II to the receptor in the presence of the $hAT_1$ receptor of the present invention and Ang II as the ligand. Since thus obtained animal cells of the present invention specifically express the human Ang II type 1 receptor of human origin, they make it possible to accurately determine the bioactivity of an antagonist or agonist against said receptor. It is also possible to reproduce in such animal cells the status of signal transduction in response to the ligand for the receptor, i.e., behavior of intracellular substances [e.g., Ca ion concentration change, cAMP concentration change, $IP_3$ (inositol triphosphate) concentration change], and obtain accurate measurements of the mounts of intracellular substances (e.g., Ca ions, cAMP, $IP_3$) or changes therein in said animal cells. A $hAT_1$ receptor agonist can be screened by a method which comprises screening a substance capable of changing an mount or a concentration of these ligand responsive substances intracellularly existing in an animal cell comprising the polypeptide of the present invention. And, an Ang II substance including a $hAT_1$ receptor antagonist can be screened by a method which comprises screening a substance, in the presence of an animal cell comprising the polypeptide of the present invention and a known ligand of the receptor such as Ang II, which is capable of inhibiting the changes of the substance intracellularly existing in the cell in response to the ligand for the receptor. Especially, when the anti-Ang II substance is $hAT_1$ receptor antagonist, the competitive inhibition would be shown in the screening. In this regard, the substance exhibiting the binding ability against the receptor in the ligand binding test is a suitable sample to supply to these screening to obtain the agonist or antagonist of the $hAT_1$ receptor.

Thus, the anti-Ang II substance, especially $hAT_1$ receptor antagonist, can be screened with high quality by the method of the present invention.

Also, the $hAT_1$ receptor can be used as an Ang II-masking protein. The transformant obtained according to the present invention, which expresses the $hAT_1$ receptor, and parts thereof can be efficiently used as an antigen to obtain antibodies against said receptor, whereby the distribution, content and other aspects of the Ang II type 1 receptor, present in trace mounts in vivo, can be determined by the fluorescent antibody method, western blotting method and other methods.

Meantime, the new recombinant DNA obtained in accordance with the present invention can be used as a probe to determine the content of the human Ang II type 1 receptor, present in trace amounts in vivo, by the northern blotting method and other method.

Abbreviations for bases, amino acids, solvents and others used in the present specification and drawings attached thereto are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise stated. These abbreviations may represent residues of corresponding compounds capable of forming a peptide bond.

DNA : Deoxyribonucleic acid
cDNA : Complementary deoxyribonucleic acid
A : Adenine
T : Thymine
G : Guanine
C : Cytosine
RNA : Ribonucleic acid
mRNA : Messenger ribonucleic acid
dATP : Deoxyadenosine triphosphate
dTTP : Deoxythymidine triphosphate
dGTP : Deoxyguanosine triphosphate
dCTP : Deoxycytidine triphosphate
ATP : Adenosine triphosphate
EDTA : Ethylenediaminetetraacetic acid
SDS : Sodium dodecyl sulfate
Gly or G : Glycine
Ala or A : Alanine
Val or V : Valine
Leu or L : Leucine
Ile or I : Isoleucine
Ser or S : Serine
Thr or T : Threonine
Cys or C : Cysteine
Met or M : Methionine
Glu or E : Glutamic acid
Gln or Q : Glutamine
Asp or D : Aspartic acid
Lys or K : Lysine
Arg or R : Arginine
His or H : Histidine
Phe or F : Phenylalanine
Tyr or Y : Tyrosine
Trp or W : Tryptophan
Pro or P : Proline
Asn or N : Asparagine

EXAMPLES

The present invention is hereinafter described in more detail by means of the following examples, which are not to be construed as limitative to the present invention.

The transformant *Escherichia coli* MC1061/P3/pHARp206 obtained in the following Example 4 has been deposited under accession number of IFO 15279 at the Institute for Fermentation, Osaka (IFO) since Mar. 31, 1992 and under accession number of FERM BP-3831 at the Fermentation Research Institute (FRI), Agency of Industrial Science and Technology, Ministry of International Trade and Industry since Apr. 13, 1992.

Example 1: Search for Well-Conserved Region at Nucleotide Sequence Level in Bovine Ang II Type 1 Receptor and Rat Ang II Type 1 Receptor A search was conducted for a homologous portion in the reported nucleotide sequences for the Ang II type 1 receptor from bovine adrenal zona glomerulosa cells [K. Sasaki et al., Nature, 351, 230 (1991)] and for the Ang II type 1 receptor from rat aortic smooth muscle cells [T. J. Murphy et al., Nature, 351, 233 (1991)]. The nucleotide sequence corresponding to Phe 39 through Tyr 127 in the amino acid sequence of the former proved much better conserved than any other portion. To amplify this well-conserved region by PCR, two primers were synthesized:

Sense primer No. 1, corresponding to Phe 39 through Asn 46:

 (SEQ ID No. 3)

Antisense primer No. 2, corresponding to Cys 121 through Tyr 127:

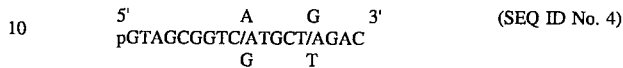 (SEQ ID No. 4)

Example 2: Amplification of Well-Conserved Region from cDNA Library of Human Placenta Origin by PCR and Nucleotide Sequencing 1 µl of a solution of a cDNA library of human placenta origin, λgt11 (CLONTECH Laboratories, Inc.) and 9 µl of distilled water were mixed. After incubation at 95° C. for 5 minutes, the mixture was immediately cooled in ice. Two primers (Nos. 1 and 2 above, 100 pmol of each) were added, and PCR was carried out as directed in the instruction manual for the kit supplied by Cetus/Perkin-Elmer, in which a series of reactions at 94° C. for 1 minute, 55° C. for 2 minutes and 72° C. for 3 minutes was repeated for 25 cycles. The PCR product was separated by 1.2% agarose gel electrophoresis; an amplified DNA fragment was seen at a position corresponding to the size (267 bp) expected from the nucleotide sequence for the Ang II type 1 receptor of bovine origin.

To the above PCR product (about 100 µl), 10 µl of a 3 M sodium acetate solution and 250 µl of ethanol were added to precipitate the DNA, which was dissolved in 10 µl of distilled water. Using 1 µl of this PCR product solution, the PCR product was inserted to the T-projection on the 3'-terminal of the pCR (trademark) vector by the action of T4 DNA ligase and ATP, in accordance with the method described in the instruction manual for the TA cloning kit (produced by Invitrogen, Corp.). The nucleotide sequence of the cDNA portion was determined using an automatic nucleotide sequencer (produced by Applied Biosystems, Inc.) based on the "dideoxy" chain termination method [J. Messing et al., Nucleic Acids Research, 9,309 (1981)]. The DNA fragment was found to contain a well-conserved region for Ang II type 1 receptor gene clearly different from either of the reported sequences of bovine and rat origins. The reported human chromosomal Ang II type 1 receptor gene [H. Furuta et al., Biochemical and Biophysical Research Communications, 183, 8 (1992)] was also found to contain a portion corresponding to this well-conserved region.

The plasmid containing this cDNA fragment was named pHARp101.

Example 3: Obtaining Full-Length Human Ang II Type 1 Receptor Gene by Plaque Hybridization Using Human Ang II Type 1 Receptor Gene Fragment The EcoRI-HindIII fragment, containing the cDNA portion, of the above-described plasmid pHARp101 was labeled with $^{32}$P and used as a probe. Then, a cDNA library from human placenta was developed over 10 plates at about 40,000 plaques/plate and replicated onto a nitrocellulose membrane (S & S), followed by plaque hybridization using the probe. Hybridization was conducted in a solution containing 6× SSC, 5× Denhardt's solution, 1% SDS and 100 µg/ml denatured bovine thymic DNA while incubating at 65° C. for 1 day. Washing was conducted in a 0.1× SSC solution containing 0.05% SDS while incubating at 68° C. for 1 hour.

Six plaques (λHARp101 through 106) that hybridized with the probe were thus obtained. Of the six clones thus obtained, λHARp106 contained the longest cDNA fragment, which cDNA portion was inserted to the EcoRI site of pUC118, the resulting plasmid being named the plasmid pHARp116. The nucleotide sequence of the cDNA portion was determined, using an automatic nucleotide sequencer (produced by Applied Biosystems, Inc.), based on the dideoxynucleotide synthetic chain termination method. The nucleotide sequence and the amino acid sequence deduced therefrom are given in FIG. 1 (SEQ. ID No. 5) and FIGS. 2A–2B (SEQ. ID No. 6), respectively. The amino acid sequence deduced from this cDNA proved highly homologous with the reported bovine, rat and human receptor sequences, suggesting that it is a typical feature of G protein-coupled receptor like these receptors. However, the present receptor was found to be a human Ang II type 1 receptor polypeptide of a new sequence, clearly different from any known sequence. It is conjectured that the $hAT_1$ receptor obtained here belongs to a subtype different from that of the reported human Ang II type 1 receptor [H. Furuta et al., Biochemical and Biophysical Research Communications. 183, 8 (1992)].

Example 4: Preparation of Recombinant DNA for Rxpression in Animal Cells of Full-Length Ang II Type 1 Receptor Gene from Human Placenta (1)

After the above plasmid pHARp116 was digested with restriction enzyme EcoRI, a fragment containing the cDNA portion was recovered by agarose electrophoresis. Then, pcDNA I, a derivative from the vector pCDM8 (Invitrogen, Corp.) [B. Seed et al. Nature, 329, 840 (1987)], used for transient expression in animal cells, was digested with restriction enzyme EcoRI, and the resulting fragment was ligated to the above DNA fragment by the action of T4 DNA ligase and ATP, followed by transformation into *Escherichia coli* MC1061/P3, to yield *Escherichia coli* MC1061/P3/pHARp206 (IFO 15279, FERM BP-3831 ), carrying the desired expression vector pHARp206.

Example5: Expression of Full-Length Ang II Type 1 Receptor Gene from Human Placenta in Animal Cells (1)

To each of two collagen-treated slide glasses (1×4 cm) in a 6 cm petri dish, 4 ml of an ASF104 medium (produced by Ajinomoto) containing 5% (v/v) FCS (fetal calf serum) was added, and 5×10$^5$ CHOdhfr⁻ cells were seeded. After incubation at 37° C. in the presence of 5% carbon dioxide for one day, the medium was aspirated and twice washed with ASF104 medium. 5 μg of the above plasmid pHARp206 was dissolved in 50 μl of HBS buffer (8.0 g/l sodium chloride, 380 mg/l potassium chloride, 200 mg/l disodium monohydrogen phosphate, 5.9 g/l HEPES, 15 mg/l calcium chloride dihydrate, 10 mg/l magnesium chloride hexahydrate, pH 7.45). The resulting solution was mixed with 50 μl of a DEAE-dextran solution (20 g/l DEAE-dextran, 9.0 g/l sodium chloride), and this mixture was added to the cells drop by drop uniformly, to yield CHOdhfr⁻ cells transformed with the plasmid pHARp206 (CHOdhfr⁻/pHARp206). To these transformant cells, 20 μl of a chloroquine solution (5.2 g/l chloroquine diphosphate) was added, followed by incubation at 37° C. in the presence of 5% carbon dioxide for 30 minutes. After the medium was aspirated, 4 ml of an ASF104 medium containing 5% FCS was added, followed by three more days of incubation under the same conditions as above.

Example 6: Change in Intracellular Calcium Ion Concentration in Response to Ang II Administration in Animal Cells Expressing Full-Length Ang II Type 1 Receptor Gene from Human Placenta After the above transformant cells CHOdhfr⁻/pHARp206 were twice washed with HEPES buffer (140 mM sodium chloride, 5 mM potassium chloride, 1 mM magnesium sulfate, 1 mM disodium monohydrogen phosphate, 1 mM calcium chloride, 25 mM glucose, 25 mM HEPES; pH 7.2), 4 ml of a HEPES buffer containing 4 μM Fura-2AM (Dojin Kagaku) was added, and the mixture was kept standing at 15° C. in the dark for 80 minutes. After being thrice washed with HEPES buffer, the mixture was further kept standing at 15° C. in the dark for 20 minutes. A quartz cuvette (1×1×4 cm) was set to a HITACHI fluorophotometer model F-4000, a stirring rod was placed therein, and 2.5 ml of a HEPES buffer containing 0.05% (w/v) BSA was added. After equilibration at 37° C., the transformant cells, along with the slide glass, were inserted to the cuvette. Fluorescence at a wavelength of 505 nm, generated upon excitation with ultraviolet rays of wavelengths of 340 nm and 380 nm, was measured. After fluorescence stabilized, Ang II was added to a final concentration of 1 μM. Several seconds later, a change in fluorescence resulting from an increase in intracellular Ca ion concentration was seen.

Similarly, endothelin 1 at the same concentration was added, but no change occurred in fluorescence. In the control experiment, no change occurred in fluorescence in non-transformed CHOdhfr⁻ cells or CHOdhfr⁻ cells transformed with the above-described plasmid pcDNA I.

Example 7: Preparation of Recombinant DNA for Expression of Full-Length Ang II Type 1 Receptor Gene from Human Placenta in Animal Cells (2)

After the above plasmid pHARp116 was digested with restriction enzyme EcoRI, a fragment containing the cDNA portion was recovered by agarose electrophoresis. Then, pTB701 [vector resulting from C kinase gene removal from the plasmid pTB652 reported by Y. Ono et al. in Science, 236, 1116–1120 (1987)], used for transient expression in animal cells, was digested with restriction enzyme EcoRI, and the resulting fragment was ligated to the above DNA fragment by the action of T4 DNA ligase and ATP, followed by transformation into *Escherichia coli* JM109, to yield *Escherichia coli* JM109/pHARp306, carrying the desired expression vector pHARp306.

Example 8: Expression of Full-Length Ang II Type 1 Receptor Gene from Human Placenta in Animal Cells (2)

To each well of a 6 well petri dish, 2 ml of a DMEM medium (produced by DIFCO) containing 5% (v/v) FCS was added, and 5×10$^4$ COS7 cells were seeded. After incubation at 37° C. in the presence of 5% carbon dioxide for two days, the medium was aspirated and twice washed with DMEM medium. Using 3 μg of the above plasmid pHARp306, the cells were transformed in accordance with the method described in Example 5, to yield transformant cells COS7/pHARp306.

Example 9: Radio-labeled Ang II Binding Activity in Animal Cells Expressing Full-Length Ang II Type 1 Receptor Gene from Human Placenta After the above transformant cells COS7/pHARp306 were twice washed with TSMB buffer (50 mM Tris buffer, pH 7.5, 150 mM sodium chloride, 5 mM magnesium chloride, 0.2% (w/v) BSA, 40 µg/ml bacitracin, 4 µg/ml leupeptin, 4 µg/ml chymostatin, 4 µg/ml pepstatin A, 5 µM phosphoramidon), 1 ml of a TSMB buffer containing a 100 pM ligand ($[^{125}I]$-labeled Ang II, 2000 Ci/mmol, produced by Amersham) was added, and the mixture was kept standing at room temperature for 60 minutes. After the mixture was thrice washed with TSMB buffer, cells were solubilized with 1 N sodium hydroxide (1 ml), and their radioactivity was determined using a γ-ray counter. At the time of ligand binding, 10 µM of each agonist (Ang I, Ang II, Ang III) and 10 µM of each antagonist (DuP753, PD123177 [P.B-.M.W.M. Timmermans et al., TiPS, 12, 55 (1991)] were also present concurrently. It was found that an Ang II type 1 receptor was expressed in the transformant cells (COS7/pHARp306) (see Table 1).

TABLE 1

| Agonist or antagonist added | Radioactivity (cpm) |
| --- | --- |
| None (control) | 84,148 |
| 10 µM Ang I | 2,326 |
| 10 µM Ang II | 676 |
| 10 µM Ang III | 670 |
| 10 µM DuP753 | 1,246 |
| 10 µM PD123177 | 69,980 |

Example 10: Obtainment of Animal Cell Line Stably Expressing Full-Length Ang II Type 1 Receptor Gene from Human Placenta To $1\times10^5$ CHOdhfr$^{31}$ cells grown on a plate of 6 cm diameter, 5 µg of pHARp306 and 0.5 µg of pTB348, a plasmid that expresses the dhfr gene, were introduced using the Transfectum reagent (Wako Pure Chemical Industries, Ltd.). CHOdhfr$^+$ cells that grew on a DMEM medium containing 10% (v/v) dialyzed-FCS and 35 µg/ml L-proline were isolated. Using these cells, Ang II binding activity was determined by the method described in Example 9; a cell clone showing high affinity to Ang II was obtained. This clone was identified as a CHO cell line stably expressing the full-length Ang II type 1 receptor of human placental origin, designated as CHO/pHARp306, and used in the following experiments.

Also, using a solution of cDNA library λgt11 of human heart origin (CLONTECH Laboratories, Inc.), the full-length gene of Ang II type 1 receptor was obtained in accordance with the method described in Example 3, which was found to be identical to a reported receptor gene of the same type [H. Furuta et al., Biochemical Biophysical Research Communications, 183, 8 (1992)]. This gene was inserted to pTB701, in accordance with the method of Example 7, to yield the expression plasmid pHARt306, which was then introduced to CHOdhfr$^-$ cells as described above to establish a CHO line stably expressing the full-length Ang II type 1 receptor gene of human heart origin, designated as CHO/pHARt306, and used as control in the following experiments.

Figure 4:
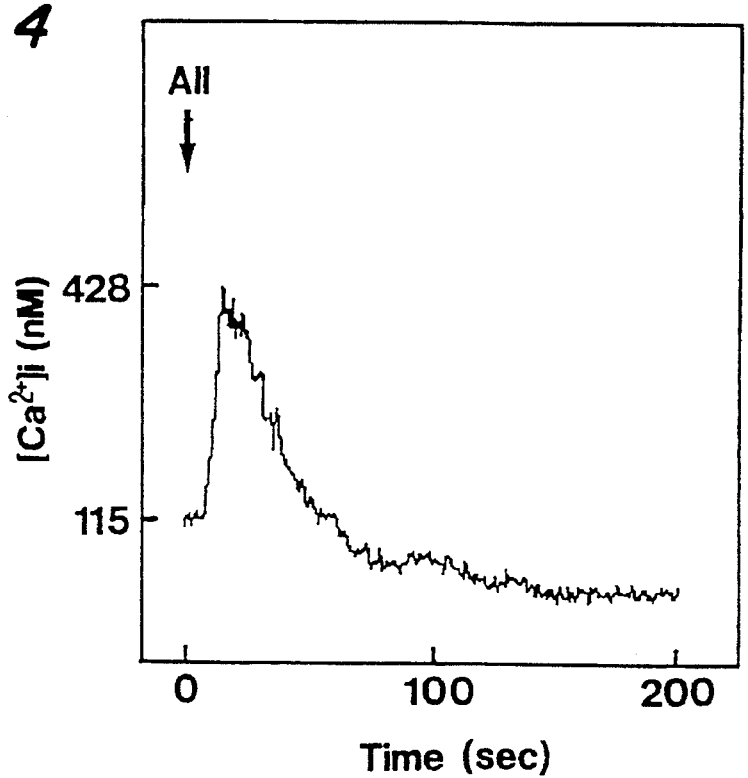
FIG. 4 shows changes in intracellular calcium ion concentration in response to stimulation with Ang II in full-length placenta-derived Ang II type 1 receptor expressing cells (see Example 11).

Example 11: Changes in Intracellular Calcium Ion Concentration in Response to Stimulation with Ang II in CHO Cells (CHO/pHARp306) Stably Expressing the Full-Length Ang II Type 1 Receptor Gene of Human Placental Origin Changes in intracellular calcium ion concentration in response to stimulation with Ang II (final concentration 100 nM) in the above stably expressing line (CHO/pHARp306) were measured in accordance with the method of Example 6; a rapid rise in concentration occurred, followed by a decline to the pre-administration level 1 minute after stimulation (see FIG. 4). At the same time, CHO/pHARt306 was examined; a rapid rise in concentration and subsequent sustained higher levels over a period of several minutes following stimulation were noted (see FIG. 3). This finding suggests that the Ang II type 1 receptor of human placental origin acts on the calcium ion channel in a mode different from that for the reported Ang II type 1 receptor.

Figure 5:
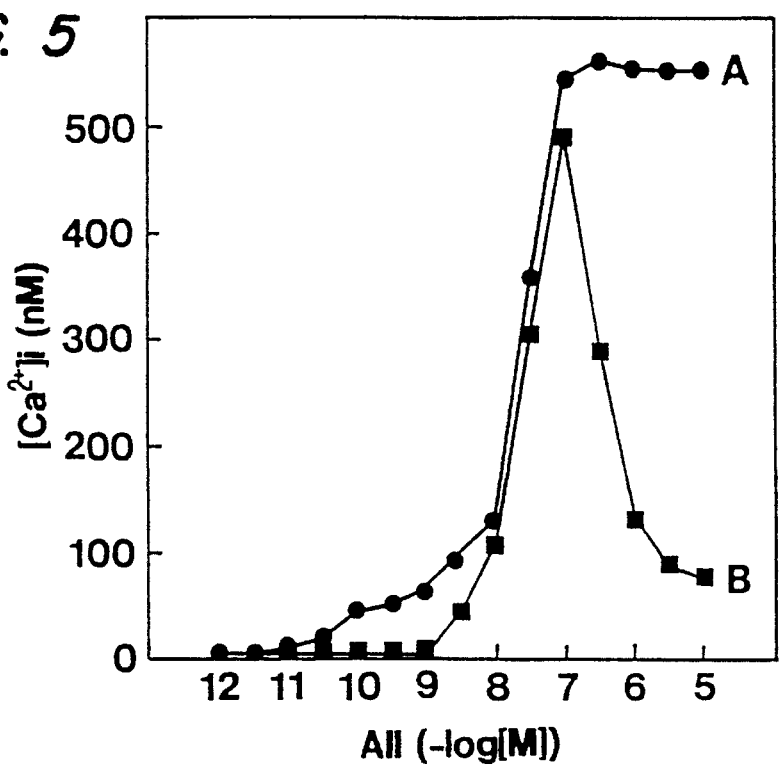
FIG. 5 shows the dose-response curve of intracellular calcium ion concentration to stimulation with Ang II in full-length Ang II type 1 receptor expressing cells.

Using the same assay system as above, the maximum change in intracellular calcium ion concentration was thrice measured at final Ang II concentrations of 1 pM to 10 µM. Unlike the reported Ang II type 1 receptor (see FIG. 5A), the Ang II type 1 receptor of the present invention (see FIG. 5B) was subject to specific inhibition of intracellular calcium ion concentration change at high concentrations of Ang II.

Example 12: Changes in Intracellular Inositol Phosphate (IPs) Concentration in Response to Stimulation with Ang II in CHO Cells (CHO/pHARp306) Stably Expressing the Full-Length Ang II Type 1 Receptor Gene of Human Placental Origin To each well of a 12 well petri dish, a DMEM medium containing 10% (v/v) dialyzed-FCS and 35 µg/ml L-proline was added, and $1\times10^5$ CHO/pHAR306 cells were inoculated. One day later, the medium was replaced with the same medium but containing 1 µCi/ml [$^3$H]-labeled inositol (Amersham), and cultivation was continued for 24 hours. The petri dish was twice washed with a PBS buffer (FLOW Laboratories) containing 0.2% (w/v) BSA and then kept standing for 30 minutes, after which it was kept standing at 37° C. for 30 minutes in the presence of the same buffer but containing 10 mM lithium chloride. Then, Ang II was added to a final concentration of 100 nM, and the petri dish was kept standing at 37° C. for a given period of time. When the reaction time exceeded 30 seconds, the reaction mixture was removed using an aspirator, after which 1 ml of a 5% (w/v) trichloroacetic acid solution was added to each well to stop the reaction. When the reaction time was 5 to 30 seconds, 1 ml of a 10% (w/v) trichloroacetic acid solution was injected directly to each well to stop the reaction. The [$^3$H]-labeled inositol phosphate (IPs) was separated using ion exchange column AG 1-X8 (Bio-Rad Laboratories). Specifically, inositol monophosphate (IP1), inositol diphosphate (IP2) and inositol triphosphate (IP3) were eluted with 5 mM disodium tetraborate and 0.18 M sodium formate, with 0.1 M formic acid and 0.4 M ammonium formate, and with 0.1 M formic acid and 1.0 M ammonium formate, respectively. The radioactivity of each fraction was determined using a liquid scintillation counter.

Figure 6:
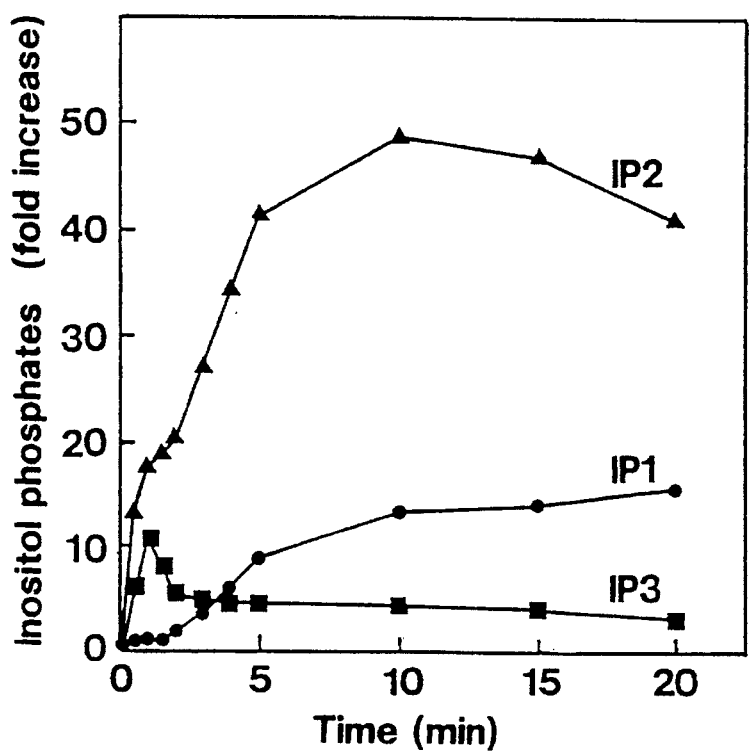
FIG. 6 shows changes in intracellular inositol phosphate concentration in response to stimulation with Ang II in full-length Ang II type 1 in receptor expressing cells.

In response to stimulation with Ang II, a transient rise in IP3 concentration occurred, followed by formation of IP2 and IP1 in this order (see FIG. 6). Control CHO/pHARt306 cells exhibited the same IPs production pattern as with CHO/pHARp306 cells.

Figure 7:
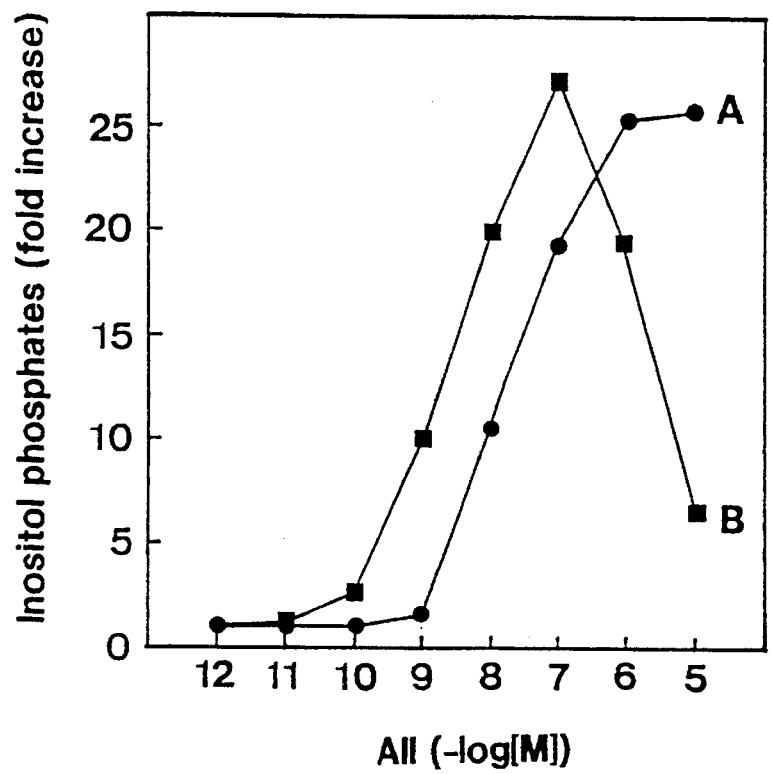
FIG. 7 shows the dose-response curve of intracellular inositol-phosphate concentration to stimulation with Ang II in full-length Ang II type 1 receptor expressing cells.

Then, using the same assay system as above, total IPs production following 20 minutes after stimulation was thrice measured at final Ang II concentrations of 1 pM to 10 µM. IPs production was suppressed in response to stimulation with high concentrations of Ang II in CHO/pHARp306 cells (see FIG. 7B). At the same time, control CHO/pHARt306 cells were tested, but IPs production was not suppressed even in the presence of high concentrations of Ang II (see FIG. 7A). This demonstrates that the Ang II type 1 receptor of the present invention, unlike the reported Ang II type 1 receptor, is subject to specific inhibition of IPs production at high concentrations of Ang II.

Example 13: Changes in Intracellular Cyclic Adenosine Monophosphate (cAMP) Concentration in Response to Stimulation with Ang II in CHO Cells (CHO/pHARp306) Stably Expressing the Full-Length Ang II Type 1 Receptor Gene of Human Placental Origin To each well of a 24 well petri dish, a DMEM medium containing 10% (v/v) dialyzed FCS and 35 µg/ml L-proline was added, and 1×10$^5$ CHO/pHAR306 cells were inoculated. Two days later, the petri dish was twice washed with a PBS buffer (FLOW Laboratories) containing 0.2% (w/v) BSA and 1 mM 3-isobutyl-1-methylxanthine (IBMX) and then kept standing at 37° C. for 20 minutes, after which Ang II was added to a final concentration of 100 nM, and the petri dish was kept standing at 37° C. for 10 minutes. After the reaction mixture was removed using an aspirator, 500 µl of a 5% (w/v) trichloroacetic acid solution was added to each well to stop the reaction. The amount of cAMP was measured by EIA (cAMP enzyme immunoassay system, produced by Amersham). At the same time, using control CHO/pHARt306 cells, changes in intracellular cAMP concentration in response to stimulation with Ang II were measured. In either type of cells, the cAMP concentration remained unchanged even in the presence of stimulation with Ang II.

Figure 8:
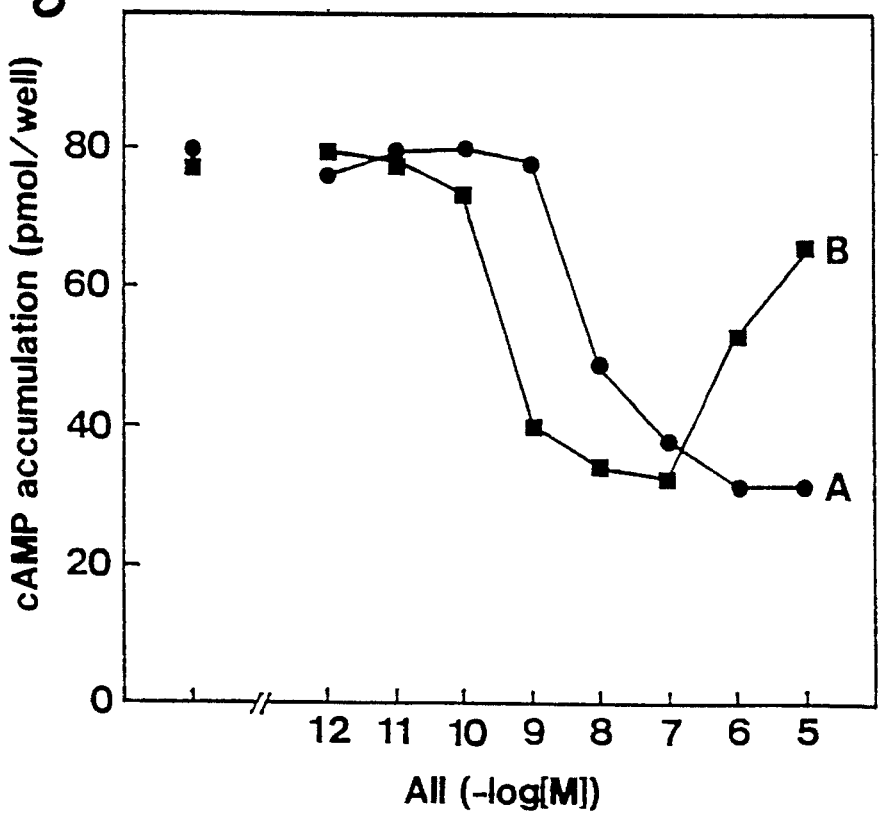
FIG. 8 shows changes in intracellular cyclic AMP concentration in response to stimulation with Ang II in full-length Ang II type-1 receptor expressing cells.

Then, using the same assay system as above but 10 µM forskolin was used as stimulant in place of Ang II, intracellular adenylate cyclase was activated, resulting in the formation of about 80 pmol/well cAMP in both types of cells. Separately, cells were stimulated with both 1 pM to 10 µM Ang II and 10 µM forskolin simultaneously, and total cAMP production was thrice measured 10 minutes later. Control CHO/pHARt306 cells were subject to cAMP production suppression depending on Ang II concentration (see FIG. 8A). On the other hand, CHO/pHARp306 cells had no suppression of cAMP production upon stimulation with high concentrations of Ang II, though they showed the same pattern of cAMP production suppression as with control cells, in response to stimulation with low concentrations of Ang II (see FIG. 8B).

Example 14: Determination of Binding Activity of Radiolabeled Ang II Using Membrane Fraction of Animal Cells Stably Expressing the Full-Length Ang II Type 1 Receptor Gene of Human Placental Origin A cell membrane fraction was extracted from the stably expressing line described in Example 10 (CHO/pHARp306), in accordance with the method described in the Journal of Pharmacology and Experimental Therapeutics, 244, 571 (1988), and stored at −80° C. until using for determination of binding activity. All measurements were performed in a series of three runs. Nonspecific binding was defined as the amount of binding in the presence of 1 µM Ang II. An aliquot of membrane fraction equivalent to 10 µg of protein was suspended in a 0.1% (w/v) BSA solution containing 25 mM Tris (pH 7.6) and 5 mM magnesium chloride, to yield a 194 µl suspension. To this suspension were added a 5 µl sample and 1 µl of [$^{125}$I]-labeled Ang II (Amersham), and the mixture was kept standing at 22° C. After 45 minutes of reaction, the reaction mixture was aspirated onto a glass filter, which was washed with 4 ml of ice-cooled Tris (pH 7.6), and the residual radioactivity on the glass filter was measured using a γ-ray counter. The final sample concentration was varied over a range of from 1 pM to 10 µM. In the measurement, the amount of non-specific binding was defined as 0%, and the maximum amount of binding in the absence of sample defined as 100%. With this regard, the − log (M) value of the sample concentration (M) resulting in 50% binding was defined as IC$_{50}$ value. A membrane fraction was also extracted from control CHO/pHARt306 cells in the same manner as above, and assayed using the same assay system. The samples used were Ang I, Ang II and Ang III as agonists, and DuP753, PD123177 (described above, see Example 8), CV-11974 (Working Example 2 and Table 3 for EP 459136), CV-12843 (Working Example 38 for EP445811) and CV-12426 (Working Example 22 for EP 483683) as antagonists.

The Ang II type 1 receptor of human placental origin (see Table 2B) was shown to have a ligand binding site different in affinity from that of the reported Ang II type 1 receptor of human heart origin (see Table 2A).

TABLE 2

| Sample | | Competition; IC$_{50}$ [−log(M)] | |
| --- | --- | --- | --- |
| | | A | A |
| Agonist | AI | 6.44 | 6.99 |
| | AII | 9.75 | 10.18 |
| | AIII | 7.57 | 9.07 |
| Antagonist | DuP753 | 8.11 | 7.48 |
| | PD123177 | <6.00 | 5.49 |
| | CV-11974 | 9.48 | 9.61 |
| | CV-12843 | 8.32 | 6.62 |
| | CV-12426 | 6.10 | 8.46 |

What is claimed is:

1. An isolated angiotensin II type 1 receptor polypeptide comprising the amino acid sequence shown in SEQ ID NO: 6.

2. A method of screening a substance for angiotensin II receptor-modulatory activity, comprising the steps of contacting an angiotensin II type 1 receptor polypeptide according to claim 1 with a candidate modulatory substance in the presence of angiotensin II; and determining whether said substance inhibits the binding of angiotensin II to said receptor polypeptide relative to a control performed in the absence of said substance.

3. A method according to claim 2, wherein the substance is an angiotensin II type 1 receptor antagonist.

4. A method of screening a substance for angiotensin II receptor-binding activity, comprising the steps of contacting an angiotensin II type 1 receptor polypeptide according to claim 1 with a candidate receptor-binding substance; and determining whether said substance binds to said receptor polypeptide.

5. A method according to claim 4, wherein the substance is an angiotensin II type 1 receptor agonist.

6. A method according to claim 4, wherein the substance is an angiotensin II type 1 receptor antagonist.

7. A method of screening a substance for angiotensin II receptor-modulatory activity, comprising the steps of providing a transformed host cell expressing heterologous DNA which encodes an angiotensin II type 1 receptor polypeptide according to claim 1, wherein said host cell comprises one or more detectable species, the concentration(s) of which are responsive to the binding of angiotensin II to said receptor;

contacting said host cell with a candidate modulatory substance in the presence of angiotensin II; and determining whether said substance induces a change in the concentration(s) of said species relative to their concentration(s) in a control cell incubated in the absence of said substance.

8. A method according to claim 7, wherein the substance is an angiotensin II type 1 receptor agonist.

9. A method according to claim 7, wherein the substance is an angiotensin II type 1 receptor antagonist.

10. A method according to claim 7, wherein said transformed host cell is an animal cell.

11. A method according to claim 7, wherein said detectable species comprise calcium ions, cAMP, or inositol triphosphate.

12. A method according to claim 7, wherein said heterologous DNA comprises the sequence shown in SEQ ID NO: 2.

13. A method according to claim 12, wherein said heterologous DNA comprises the sequence shown in SEQ ID NO: 5.

* * * * *